(12) United States Patent
Hsu et al.

(10) Patent No.: US 7,001,756 B1
(45) Date of Patent: Feb. 21, 2006

(54) **MICROORGANISM STRAIN OF GM-020 OF *LACTOBACILLUS RHAMNOSUS* AND ITS USE FOR TREATING OBESITY**

(75) Inventors: Ching-Hsiang Hsu, Tainan County (TW); Wei-Chih Su, Tainan County (TW)

(73) Assignee: GenMont Biotech Inc., (TW)

( * ) Notice: Subject to any disclaimer, the term of this patent is extended or adjusted under 35 U.S.C. 154(b) by 0 days.

(21) Appl. No.: 10/780,601

(22) Filed: Feb. 19, 2004

(51) Int. Cl.
*C12N 1/20* (2006.01)
*A01N 63/00* (2006.01)
*A61K 39/00* (2006.01)

(52) U.S. Cl. .................. 435/252.9; 424/93.1; 424/93.2; 424/93.45; 424/184.1

(58) Field of Classification Search ............ 424/93.45, 424/93.1, 93.2, 184.1; 435/252.9
See application file for complete search history.

(56) References Cited

U.S. PATENT DOCUMENTS 6,214,336 B1 * 4/2001 Bukowska et al. ...... 424/93.45

FOREIGN PATENT DOCUMENTS

| WO | WO 99/07827 | * | 2/1999 |
| WO | WO 99/10476 | * | 3/1999 |

OTHER PUBLICATIONS

Tamki et al (Mokuzai Gakkaishi, Mar. 1997, vol. 43, No. 1, p. 90-95). Abstract only.*
Yang et al (Biotechnology Letters, Aug. 2002, Vo. 24, No. 16, p. 1319-1325).*
Agerholm-Larsen et al, European Journal of Clinical Nutrition, 2000.*
Usman et al. (2001) Hypocholesterolemic effect of *Lactobacillus gasseri* SBT0270 in rats fed a cholesterol-enriched diet. *J. Dairy Res.* 68: 617-624.
Zhou et al. (2000) Safety assessment of potential probiotic lactic acid bacterial strains *Lactobacillus rhamnosus* HN001, *Lb. acidophilus* HN017, and *Bifidobacterium lactis* HN019 in BALB/c mice. *International Journal of Food Microbiology* 56: 87-96.
Agerholm-Larsen et al. (2000) Effect of 8 week intake of probiotic milk products on risk factors for cardiovascular diseases. *Eur J Clin Nutr.* 54(4): 288-97.
Gordon et al. (1989) High-density lipoprotein cholesterol and cardiovascular disease. *Circulation.* 79:8-15.

* cited by examiner

*Primary Examiner*—Mark Navarro
*Assistant Examiner*—Vanessa L. Ford
(74) *Attorney, Agent, or Firm*—Banner & Witcoff, Ltd.

(57) ABSTRACT

The present invention provides an isolated microorganism strain, *Lactobacillus rhamnosus* GM-020, which is found to be effective in treating obesity and a complication thereof. The use of the *Lactobacillus rhamnosus* GM-020 in treating obesity and a complication thereof is also provided.

9 Claims, 10 Drawing Sheets

MICROORGANISM STRAIN OF GM-020 OF *LACTOBACILLUS RHAMNOSUS* AND ITS USE FOR TREATING OBESITY

BACKGROUND OF THE INVENTION

1. Field of the Invention

The invention mainly relates to a novel microorganism strain *Lactobacillus rhamnosus* GM-020 and its use for treating obesity or complications thereof.

2. Description of the Related Art

Obesity is an excess of body fat usually due to changes of physiological or biochemical function and is a significant impairment of health. Fat usually contains neutral lipids, phospholipids and cholesterols. Weight gain is dependent on a person's energy intake being greater than energy expenditure. There are two types of obesity: (a) simple obesity, and (b) secondary obesity. Simple obesity is divided into idiopathic obesity and acquired obesity; the latter accounts for more 95% of obesity. Idiopathic obesity results from a large number of fat cell, and is usually found in childhood obesity. Acquired obesity results from a larger size of fat cell, and is usually found in adult obesity. Secondary obesity is known as symptomatic obesity, usually results from endocrine or metabolic diseases. Obesity is associated with several chronic diseases, such as diabetes mellitus, cardiopathy, hypertension, apoplexy, biliary calculus, gout, and some carcinomas.

There are five strategies for treating obesity: diet, exercise, behavioral treatment, drug treatment, and therapeutic operation. The strategies are chosen or combined to treat an obesity patient depending on the patient's risk factors in health, and the rate and effect of losing weight, which are influenced by multiple factors such as age, height, family history, and risk factors. The mechanisms of drug treatment include inhibiting appetite, increasing energy expenditure, stimulating fat movement, lowering triacylglycerol synthesis, and inhibiting fat absorption. Examples of these drugs are phenylpropanolamine (PPA), orlistat (Xenical™), and sibutramine (Reductil™). However, it is a new trend to treat obesity with a natural substance, not a drug.

In the prior art, it was found that some microorganism strains could be used to treat obesity, or complications thereof. For instance, *Lactobacillus gasseri* SBT0270 was found to have an ability to lower cholesterol concentration related to deconjugate of bile acid (Usman, B. and Hosono, A. (2001) Hypocholesterolemic effect of *Lactobacillus gasseri* SBT0270 in rats fed a cholesterol-enriched diet. *J. Dairy Res.* 68: 617–624). The mechanism of treating obesity is lowering the solubility of the deconjugated bile acid through absorption of free form of bile acid by *L. gasseri* an exhaustion with stools (since the exhausted bile acid cannot be recycled back to the liver, and new bile acid is needed to be synthesized from cholesterol.) Besides, it was found that *L. gasseri* could be combined with bile acid and cholesterol to make an excretion.

*Lactobacillus rhamnosus* was regarded as a potential probiotic lactic acid bacterium that has an immune-enhancing property. Safety assessment of *L. rhamnosus* was also investigated. Zhou et al. disclosed that hematological parameters (red blood cell and platelet counts, hemoglobin concentration, mean corpuscular volume, mean corpuscular hemoglobin, and mean corpuscular hemoglobin concentration); differential leukocyte counts; blood biochemistry (plasma total protein, albumin, cholesterol, and glucose); mucosal histology (epithelial cell height, mucosal thickness, and villus height); and bacterial translocation to extra-gut tissues (blood, liver, spleen, kidney and mesenteric lymph nodes) of mice administrated with *L. rhamnosus* showed similar profiles to those of the control mice (Zhou, J. S., Shu, Q., Rutherfurd, K. J., Prasad, J., Birtles, M. J., Gopal, P. K. and Gill, H. S. (2000) Safety assessment of potential probiotic lactic acid bacterial strains *Lactobacillus rhamnosus* HN001, *Lb. acidophilus* HN017, and *Bifidobacterium lactis* HN019 in BALB/c mice. *International Journal of Food Microbiology* 56: 87–96). In addition, Agerholm-Larsen et al. disclose that administration of a yogurt fermented with *L. rhamnosus* does not change low density lipoproteins (LDL)-cholesterol. On the other hand, only systolic blood pressure was significantly reduced (Agerholm-Larsen, L., Raben, A., Haulrik N., Hansen, A. S., Manders, M., and Astrup A. (2000) Effect of 8 week intake of probiotic milk products on risk factors for cardiovascular diseases. *Eur J Clin Nutr.* 54(4): 288–97). Accordingly, the conventional *L. rhamnosus* strain is evidenced that it does not change plasma total cholesterol and LDL-cholesterol. Furthermore, no body weight change is observed when administration of the conventional *L. rhamnosus* strains.

SUMMARY OF THE INVENTION

The invention provides a new microorganism strain *Lactobacillus rhamnosus* GM-020.

In another aspect, the invention provides a method for treating obesity and complications thereof in a subject comprising administrating said subject with a composition comprising the microorganism strain *Lactobacillus rhamnosus* GM-020; wherein the complication is preferably selected from the group consisting of hypercholesterolemia, atherosclerosis and coronary heart disease.

In still another aspect, the invention provides a method for treating obesity and complications thereof in a subject comprising administrating said subject with a composition comprising the microorganism strain *Lactobacillus rhamnosus* GM-020 and an *Auricularia polytricha* strain; wherein the complication is preferably selected from the group consisting of hypercholesterolemia, atherosclerosis, coronary heart disease, fatty liver, and diabetes mellitus.

DETAILED DESCRIPTION OF THE INVENTION

The invention provides a novel microorganism strain *Lactobacillus rhamnosus* GM-020, which is capable of treating obesity. The strain GM-020 was deposited with the China Center for Type Culture Collection (CCTCC), Wuhan University, Wuhan 230072 P.R. China, under the accession number of CCTCC M 203098 on Dec. 18, 2003.

The *Lactobacillus rhamnosus* GM-020 is isolated from human stomach.

The microbiological characteristics of the *Lactobacillus rhamnosus* GM-020 are shown below:
(a) Morphological Characteristics:
  (1) Shape and size of cell: *bacillus*, which has a rod-like shape with round edge when the cells after cultured at 37° C. overnight in MRS broth were observed with a microscope.
  (2) Motility: non-motile
  (3) Flagella: none
  (4) Sporulation: no spore-forming
  (5) Gram-stain: positive
(b) Cultural Characteristics:
  (1) Medium: MRS broth (DIFCO® 0881) (as shown in Table 1), final pH 6.5±0.2

TABLE 1

| Component | g/L |
| --- | --- |
| Proteose peptone | 10.0 |
| Beef Extract | 10.0 |
| Yeast Extract | 5.0 |
| Dextrose | 20.0 |
| Polysorbate 80 | 1.0 |
| Ammonium Citrate | 2.0 |
| Sodium Acetate | 5.0 |
| Magnesium Sulfate | 0.1 |

TABLE 1-continued

| Component | g/L |
| --- | --- |
| Manganese Sulfate | 0.05 |
| Dipotassium Phosphate | 2.0 |

(2) Cultural condition: 37° C. anaerobic or aerobic culture
(c) Physiological Characteristics:
  (1) Catalase: negative
  (2) Oxidase: negative
  (3) API 50 CHL test: API 50 CHL system is used for identification of lactic acid bacteria. By assaying the responses of a serious of enzymes, the characters of the lactic acid are established. The result of API 50 CHL test of GM-020 is listed in Table 2:

TABLE 2

| Enzyme | Response | Enzyme | Response | Enzyme | Response |
| --- | --- | --- | --- | --- | --- |
| Glycerol | − | Mannitol | + | D-Tagatos | + |
| Erythritol | − | Sorbitol | + | 5 ceto-gluconate | − |
| D-Arabinose | − | α-Methyl-D-Glucoside | + | 2 ceto-gluconate | − |
| L-Arabinose | − | N Acetyl glucosamine | + | Gluconate | − |
| Ribose | + | Amygdaline | + | L-Arabiyol | − |
| D-Xylose | − | Arbutine | + | D-Arabitol | − |
| L-Xylose | − | Esculine | + | L-Fucose | − |
| Adonitol | − | Salicine | + | D-Fucose | − |
| β-Methyl-xyloside | − | Cellobiose | + | D-Lyxose | − |
| D-Glucose | + | Galactose | + | Inuline | − |
| D-Fructose | + | Lactose | + | Saccharose | − |
| D-Mannose | + | α-Methyl-D-mannoside | − | Glycogene | − |
| L-Sorbose | + | Melezitose | + | Xylitol | − |
| Rhamnose | + | D-Raffinose | − | β Gentiobiose | − |
| Dulcitol | − | Amidon | − | D-Turanose | − |
| Inositol | − | Maltose | − | Melibiose | − |
| Trehalose | − | | | | |

Figure 1:
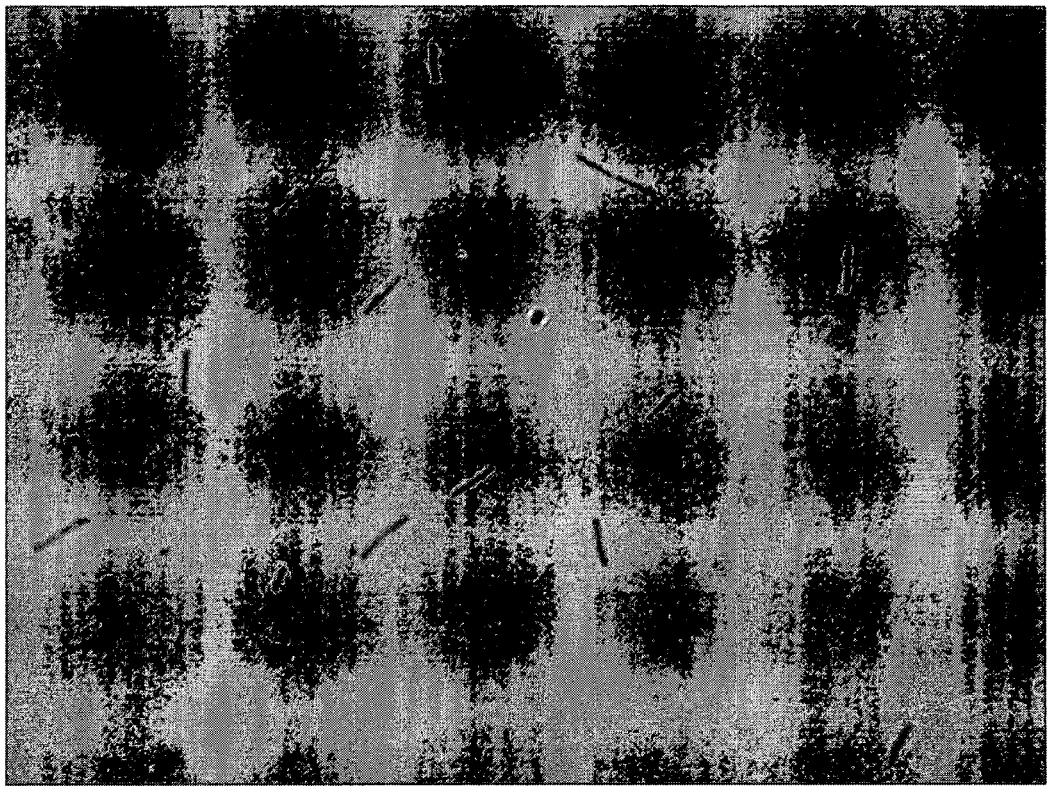
FIG. 1 illustrates the 1000× microscopic view of GM-020.
Figure 2:
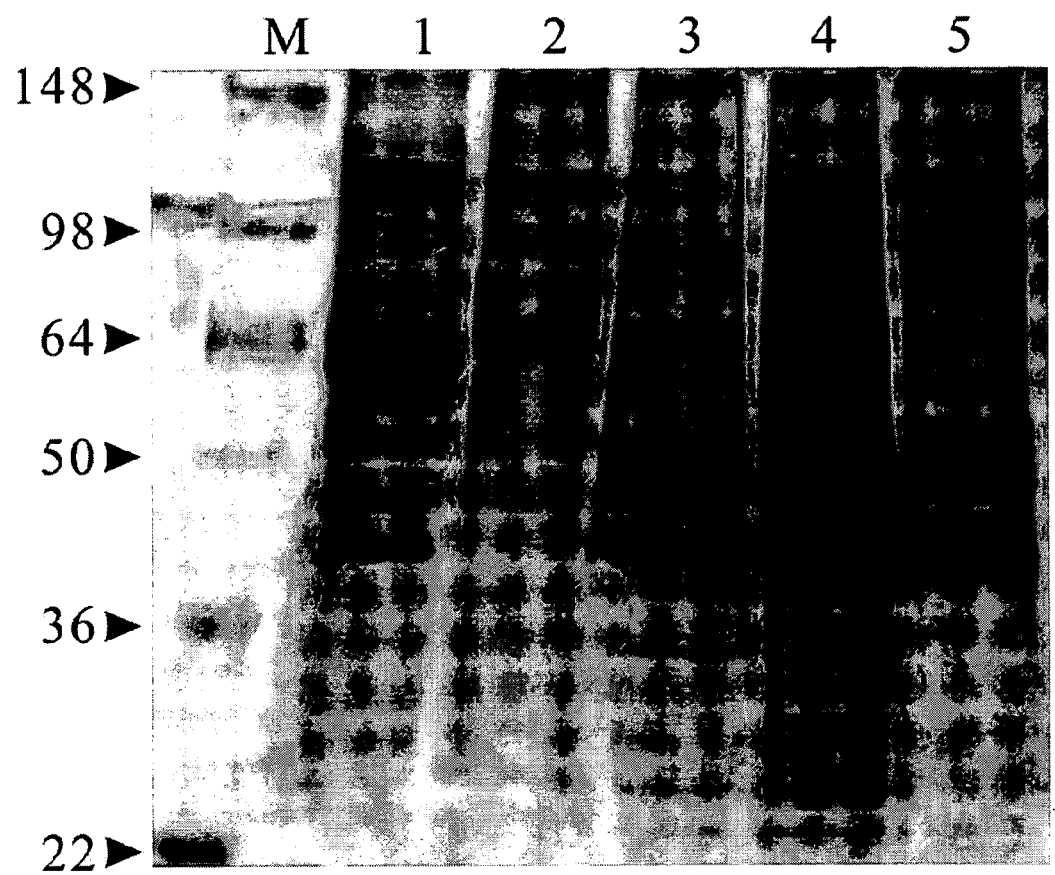
FIG. 2 illustrates the cell wall proteins of GM-020 and conventional *Lactobacillus rhamnosus* strains; wherein M represents protein molecular weight; Lane 1 represents *Lactobacillus rhamnosus* (commercial product Antibiophilus); Lane 2 represents *Lactobacillus rhamnosus* GM-020; Lane 3 represents *Lactobacillus rhamnosus* ATCC9595; Lane 4 represents *Lactobacillus rhamnosus* ATCC10940; and Lane 5 represents *Lactobacillus rhamnosus* ATCC14029.
Figure 3:
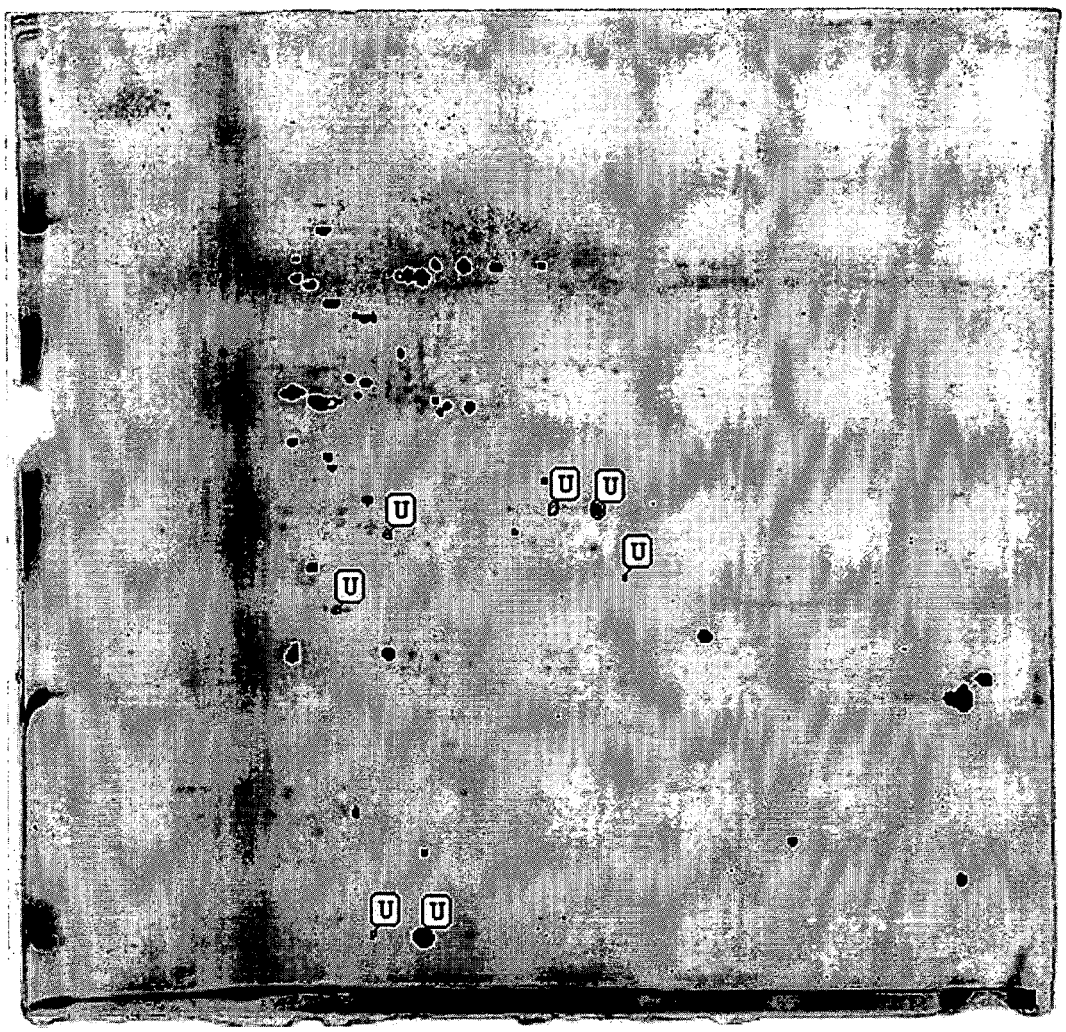
FIG. 3 illustrates the 2-D total proteins electrophoresis of GM-020.

(d) Genetic Characteristics:
  16S rDNA sequence analysis of GM-020 is determined by Food Industry Research & Development Institute, Hsin-Chu, Taiwan, R.O.C. as shown in SEQ ID NO: 1. The result shows that GM-020 is highly homologous to other *Lactobacillus rhamnosus* strains with more than 99% similarity.
(e) Cell wall proteins of GM-020:
  The cell wall proteins of GM-020 show specific pattern when compared with other conventional *Lactobacillus rhamnosus* strains. The SDS-PAGE patterns of the cell wall proteins of GM-020 are shown in FIG. 2.
  The total proteins of GM-020 are subjected to 2-D electrophoresis, and the pattern as shown in FIG. 3 is specific.
(f) Standardized detection system for identifying GM-020:
  The standard detection system for identifying microorganism is disclosed in U.S. patent application Ser. No. 10/446,781 filed on May 29, 2003, using gene expression difference of a test cell line culturing with and without a given microorganism as a marker for identification. The genes tested are listed in Table 3.

TABLE 3

Gene
Signal transducer and activator of transcription 3
c-rel
growth associated protein43
N-myc
IGF binding protein 1
IL-16
Lymphotoxin alpha (formerly tumor necrosis factor beta)
Interferon-inducible protein 9-27
Connective tissue growth factor
Interleukin 10 receptor
calpamodulin mRNA
ubiquitin conjugating enzyme (UbcH8) mRNA, comp
Homo sapiens protein kinase A binding protein AKAP110 mRNA, complete cds
pyruvate dehydrogenase kinase, isoenzyme 4
Pyridoxal (pyridoxine, vitamin B6) kinase
MAP kinase-interacting serine/threonine kinase 1
Leukocyte tyrosine kinase
Neurotrophic tyrosine kinase, receptor, type 3 (TrkC)
pyruvate dehydrogenase kinase isoenzyme 3 (PDK3) mRNA, complete cds
Human diacylglycerol kinase zeta mRNA, complete cds
Protein kinase C, alpha
Deoxyguanosine kinase
Adenosine kinase
Topoisomerase (DNA) II beta (180 kD)
IkB kinase beta subunit mRNA
stat5a(Signal transducer and activator of transcription 5A)
Colony-stimulating factor 1 (M-CSF)
HGF
IL-1 receptor type 1
Interleukin 7
metallothionein I-B gene
Interleukin 6 (B cell stimulatory factor 2)
Small inducible cytokine A2 (monocyte chemotactic protein 1,
Proteasome 26S subunit, ATPase,3
Ubiquitin-conjugating enzyme E2A (RAD6 homolog)
thymidine kinase 1, soluble
Tyrosine kinase 2
serine/threonine protein-kinase
Transforming growth factor beta-activated kinase 1
Fms-related tyrosine kinase 3
Creatine kinase B
Protein serine/threonine kinase stk2
stress-activated protein kinase 3 (SAPK3) mRNA.
Human adenylate kinase 2 (adk2) mRNA, complete cds
RAC-ALPHA SERINE/THREONINE KINASE
Hexokinase 1
CDC28 protein kinase 2 (CKS2) mRNA.
Superoxide dismutase 2, mitochondrial
Tumor necrosis factor receptor 2
Growth associated protein 43
p53-associated gene
CD30
metallothionein-III
Interleukin 4 receptor
Gamma-interferon-inducible protein ip-30 precursor
Interferon-alpha/beta receptor alpha chain precursor
Early growth response protein 1
interleukin-13 receptor mRNA, complete cds
protease inhibitor 12 (PI12; neuroserpin)
serine/threonine protein kinase KKIALRE
Phosphorylase kinase, beta
serine/threonine kinase 9
Serine/threonine kinase 10
Protein kinase mitogen-activated 8 (MAP kinase)
focal adhesion kinase (FAK) mRNA, complete cds
Human activated p21cdc42Hs kinase (ack) mRNA, complete cds
Human integrin-linked kinase (ILK) mRNA, complete cds
Human guanylate kinase (GUK1) mRNA, complete cds
BMK1 alpha kinase mRNA, complete cds
flavin containing monooxygenase 5 (FMO5) mRNA.
Pyruvate kinase, liver
transcription elongation factor S-II, hS-II-T
nitric oxide synthase 3 (endothelial cell)
Bcl2, p53 binding protein Bbp/53BP2 (BBP/53BP2) mRNA, telomeric DNA sequence
stat-like protein (Fe65) mRNA, complete cds

TABLE 3-continued

IL-5 receptor a
EGF
FGF2
Interleukin 2 receptor gamma chain
C-C CHEMOKINE RECEPTOR TYPE 2
Guanylate binding protein 1, interferon-inducible, 67 kD
mitochondrial processing peptidase beta-subunit
syntaxin 8
Cytokine suppressive anti-inflammatory drug binding protein 1 (p38 MAP kinase)
protein tyrosine kinase 6
Branched chain alpha-ketoacid dehydrogenase kinase
Serine/threonine kinase 2
protein kinase, mitogen-activated 4 (MAP kinase 4; p63)(PRKM4) mRNA.
Tyrosine-protein kinase SYK
Human putative serine/threonine protein kinase PRK (prk) mRNA, complete cds
Adenylate kinase isoenzyme 1
Hemopoietic cell kinase
Glycerol kinase
Tyrosine-protein kinase CSK
General transcription factor IIB
Interleukin 6 signal transducer (gp130, oncostatin M receptor)
Caspase-8 (Apoptotic cysteine protease mch5 (mach-alpha-1))
Tumor protein p53
Transforming growth factor, beta receptor III (betaglycan, 3
IFN-g
Transforming growth factor, beta 3
TGF-beta superfamily protein, complete
Fibroblast growth factor 7 (keratinocyte growth factor)
Small inducible cytokine A4 (homologous to mouse Mip-1b)
hepatocyte growth factor activator inh
Ubiquitin carboxyl-terminal hydrolase isozyme 11
serine/threonine kinase 11 (Peutz-Jeghers syndrome
Cyclin-dependent kinase inhibitor 3 (CDK2-associated dual specificity phosphatase)
pyruvate dehydrogenase kinase, isoenzyme 3
Carnitine palmitoyltransferase I, liver
Protein kinase mitogen-activated 7 (MAP kinase)
Human protein tyrosine kinase mRNA, complete cds
Protein-tyrosine kinase 7
Lymphocyte-specific protein tyrosine kinase
Ribosomal protein s6 kinase
src-like kinase (slk) mRNA, complete cds.
Nucleoside diphosphate kinase a
Cyclin-dependent kinase 2
STAT-1alpha/beta
Angiopoietin-1
Phospholipase C
STAT2(Signal transducer and activator of transcription 2)
c-src tyrosine kinase
IL-15
TGFb receptor associate protein 1
Annexin V (lipocortin V; endonexin II)
Interferon regulatory factor 5
interferon-gamma receptor alpha chain precursor
Transforming growth factor, beta receptor II (70–80 kD)
Homo sapiens apoptotic protease activating factor 1 (Apaf-1)
Ubiquitin-conjugating enzyme E2B (RAD6 homolog)
MAP/ERK kinase kinase 3
phosphorylase kinase, alpha 2 (liver), glycogen storage disease IX
Serine/threonine kinase 4
Glucosamine-6-phosphate deaminase
Mevalonate kinase
Glucokinase (hexokinase 4, maturity onset diabetes of the young 2)
Deoxycytidine kinase
Urokinase-type plasminogen activator
Human mitochondrial creatine kinase (CKMT) gene, complete cds
Choline kinase
Human 53K isoform of Type II phosphatidylinositol-4-phosphate 5-kinase (PIPK) mRNA, complete cds
Leukocyte adhesion protein beta subunit
c-fos
phosphoenolpyruvate carboxykinase
apoptotic cysteine protease mch4
Monocyte chemotactic protein 1
Transcription factor AP-4 (activating enhancer-binding prote
Interleukin-1 receptor, type 1 precursor TABLE 3-continued Caspase-10 (Human apoptotic cysteine protease mch4)
Human kinase (TTK) mRNA, complete cds
Beta-2 adrenergic receptor
Estrogen sulfotransferase (ste)
signal transducer and activator of transcription 6, interleukin-4 induced
Protein kinase clk1
Interleukin-8 precursor
H. sapiens mRNA for FAST kinase
Interferon-gamma receptor alpha chain precursor
Insulin-like growth factor I receptor precursor
mitochondrial transcription termination factor
Signal transducer and activator of transcription 3 (acute-ph
H. sapiens mRNA for protein kinase CK1
MAP kinase activated protein kinase
Protein kinase clk3
INF-b
General transcription factor IIB
sis, PDGF B chain
β-actin
Glutathione S-transferase M1
IL-1b
MAP/ERK kinase kinase 3
INF-b
EGR-1
Glutathione S-transferase 12 (microsomal)

The standard detection system for identifying GM-020 takes Hep G2 cell line as the test cell line. When comparing the expression patterns of culturing Hep G2 cell line with and without GM-020, the group of genes as listed in Table 4 is significantly different.

TABLE 4

Gene
Interleukin 10 receptor
IL-16
EGF
Lymphotoxin alpha (formerly tumor necrosis factor beta)
Interferon regulatory factor 5
Fibroblast growth factor 7 (keratinocyte growth factor)
Proteasome 26S subunit, ATPase,3
calpamodulin mRNA
Ubiquitin carboxyl-terminal hydrolase isozyme L1
Hexokinase 1
Human 53K isoform of Type II phosphatidylinositol-4-phosphate 5-kinase (PIPK) mRNA, complete cds
mitochondrial transcription termination factor
STAT-1alpha/beta
Urokinase-type plasminogen activator
Human adenylate kinase 2 (adk2) mRNA, complete cds
Protein kinase C, alpha
Proto-oncogene tyrosine-protein kinase FES/FPS
Human mitochondrial creatine kinase (CKMT) gene, complete cds
protein tyrosine kinase 6
serine/threonine kinase 9
IkB kinase beta subunit mRNA
Caspase-8 (Apoptotic cysteine protease mch5 (mach-alpha-1))
Bcl2, p53 binding protein Bbp/53BP2 (BBP/53BP2) mRNA,
Growth associated protein 43
Protein kinase clk3
Tumor necrosis factor-inducible protein TSG-6 precursor
Insulin-like growth factor I receptor precursor
Monocyte chemotactic protein 1
Leukocyte adhesion protein beta subunit
sis, PDGF B chain
Humig mRNA
CD27L receptor precursor
retinoic acid- and interferon-inducible 58K protein RI
IRF-1

The present invention provides a method for treating obesity and a complication thereof in a subject comprising administrating said subject with a composition comprising GM-020.

It is surprisingly found in the invention that the strain GM-020 has an ability to inhibit body weight gain in a subject even when the subject taking high energy diet, and is capable of inhibiting body weight. In one experiment according to the invention, the ICR mice fed with high energy diet to lead to obesity with a treatment of the strain GM-020, the body weight was kept without any increase, compared with the control group without treatment.

It is also found in the invention that the strain GM-020 is effective in adjusting cholesterol and lipoprotein ratios. In one experiment according to the invention, the serum and liver concentrations of total cholesterol were lowered in the obesity mice and hamsters fed with cholesterol-enriched diet to lead to hypercholesterolemia with a treatment of the strain GM-020. The serum concentration of low density lipoprotein-cholesterol (LDL-C) was also lowered. Besides, the ratio of LDL-C and high density lipoprotein-cholesterol (HDL-C) (LDL-C/HDL-C) in serum was lowered. It would be concluded that that the strain GM-020 is effective in treating hypercholesterolemia and lowering the morbidity rate of atherosclerosis and coronary heart disease. That is, the strain GM-020 can be used for preparing a composition for treating obesity and a complication thereof, such as hypercholesterolemia and lowering the morbidity rate of atherosclerosis and coronary heart disease.

The invention also provides a method for treating obesity and complications thereof in a subject comprising administrating said subject with a composition comprising the microorganism strain Lactobacillus rhamnosus GM-020 and an Auricularia polytricha strain; wherein the complication is preferably selected from the group consisting of hypercholesterolemia, atherosclerosis, coronary heart disease, fatty liver, and diabetes mellitus.

It is found in the invention that the strain GM-020 in combination with Auricularia polytricha (wood ear) provides a dramatic effect in treating obesity, compared with wood ear or the strain GM-020 solely.

Auricularia auricula, known as wood ear, tree ear, etc., is a rubbery flavorless edible fungus. It is closely relative to Auricularia polytrichia cultivated in Asia, and has been consumed for a long time. Auricularia auricula is found to grow in wild on conifers and sometimes on deciduous wood in both spring and fall seasons. Wood ear is usually dried for the preparation as food. When eating the dried wood ear, the edible fibers extend about 8 to 10 times after absorbing water. The consumer feels full and reduces eating. Furthermore, polysaccharides in wood ear were reported to have an effect in lowering the serum concentration of total cholesterol in rabbits.

In one experiment according to the invention, the body weight of the obesity animal model with a treatment with the combination of wood ear and GM-020 was reduced; in contrast, the administration of wood ear or GM-020 solely can inhibit body weight gain only.

It is found in the invention that the combination of wood ear and the strain GM-020 has an ability to lower the serum and liver concentrations of total cholesterol and triacylglycerol in the animal model compared with the control group. It is concluded that the combination of wood ear and the strain GM-020 can be used for preparing a composition for treating hypercholesterolemia, fatty liver, diabetes mellitus and lowering the morbidity rate of atherosclerosis and coronary heart disease.

In one experiment according to the invention, the effect of treating obesity and hypercholesterolemia and lowering the morbidity rate of atherosclerosis and coronary heart disease was positively correlated to the dosage of wood ear. Normally, the daily suggested dosage (1×) of wood ear in an adult is 6 g×0.0026×surface area. In one embodiment of the invention, 10× of wood ear has a better effect than 1× of wood ear.

According to the invention, the strain GM-020 alone, and the combination of GM-020 and wood ear do not harm to the liver and kidney. In the animal model, the liver function is normal when monitoring the amount of glutamic oxaloacetic transaminase (GOT), glutamic pyruvic transaminase (GPT), uric acid and creatinine, which shows that the administration of strain GM-020 alone or the combination of the strain GM-020 and wood ear, is a safe way for treating obesity and the complications thereof. It is also found in the invention that triacylglycerol in serum was reduced after the treatment of the combination of GM-020 and wood ear.

The following Examples are given for the purpose of illustration only and are not intended to limit the scope of the present invention.

EXAMPLE 1

Isolation of *Lactobacillus rhamnosus* GM-020

A piece of human stomach tissue taken by an endoscope was cultured in 2 mL of *Lactobacillus* MRS Broth (DIFCO® 0881). The broth containing the tissue was plated on *Lactobacillus* selective agar and incubated at 37° C. for one day. Single colony growing on the plate was selected and subjected to Gram-stain. Gram-positive bacteria were then selected. One strain, called as *Lactobacillus rhamnosus* GM-020, was cloned.

EXAMPLE 2

Cell Wall Proteins Extraction and Analysis of GM-020

Twenty-four-hour-old cells of mesophilic lactobacilli cultivated in MRS broth (Difco®) were harvested, washed twice in 0.05 M Tris-HCl (pH 7.5) containing 0.1 M $CaCl_2$, and resuspended in 1 ml of the same buffer at an $A_{600}$ of 10.0. After centrifugation at 8,000×g for 5 min, cell wall proteins were extracted from the pellets with 1.0 ml of extraction buffer (pH 8.0) containing 0.01 M EDTA, 0.01 M NaCl, and 2% (wt/vol) SDS. Suspensions were stored at room temperature for 60 min, heated at 100° C. for 5 min, and centrifuged at 11,600×g for 10 min at 4° C. The supernatants were analyzed by 12% SDS-PAGE and stained with Comassie blue.

EXAMPLE 3

Two-D Total Proteins Electrophoresis of GM-020

Ten mg of GM-020 cells were added with 0.5 mL of lysis buffer C (7M urea, 4% CHAPS, 2 M thiourea, 40 mM tris base, 0.5% IPG buffer amd 5 mM TBP) and 100 µL of glass beads. The solution was then subjected to sonicate and centrifuged at 10,000 rpm for 30 min. Total proteins were determined by Bio-rad PlusOne™ protein assay and then subjected to 2-D electrophoresis with pH 3 to 10 IEF. The electrophresis as programmed in Table 5 was performed with 10% gel and with 40 mA/gel for 4 hours. The gel was then fixed with 10% methanol and 7% acetic acid for 30 min. After fixation, the gel was colorized by sypro ruby stain for 5 hours and then destained with 10% methanl and 7% acetic acid for 6 hours. The result was shown in FIG. 3.

TABLE 5

| | |
|---|---|
| 30 V | 12 hr |
| 100 V | 0:10 hr |
| 250 V | 0:10 hr |
| 500 V | 0:10 hr |
| 1000 V | 0:30 hr |
| 4000 V | 0:30 hr |
| 6000 V | 60 KVhr |

EXAMPLE 4

A Standardized Detection System for Identifying GM-020

Preparation of GM-020 for a standardized detection system: The cells of the strain GM-020 were incubated in *Lactobacillus* MRS broth (DIFCO® 0881) at 37° C. to the stationary phase. After centrifuged at 3,000 g for 15 min, the culture was washed with 2 mL and 1 mL of 1× of PBS (phosphate buffered saline, pH 7.2) and then suspended in 1 mL of PBS (1×), wherein the cell concentration was adjusted to $1\times10^9$ CFU/mL. The cultures were stored at −20° C.

Stimulation: The Hep G2 cells were refreshed by adding a fresh medium and cultured for 16 hours. Subsequently, the cells were divided into two groups, and one was for the culture with the lactic acid bacteria and the other was for the culture without the lactic acid bacteria. When the cell concentration reached $1\times10^{7/0}$ mL, cells were stimulated for 24 h with or without $1\times10^7$ GM-020. After stimulation, the cells were collected, washed twice with PBS, and used for RNA isolation.

RNA isolation and labeling: RNA was extracted from cell by using Trizol Reagent (Life Technologies®, Gaithersburg, Md.) according to the manufacturer's instructions. Eight L of the RNA (10 µg) and 2 L oligo poly-dT (12–18 mer, 0.1 g/L) were well mixed and kept at 70° C. for 10 minutes and then were cooled with ice for 2 minutes. Mixed the RNA with reverse transcription labeling mixture and 3 L Cy5-dUTP (1 mM), 2 L SuperScript II (200 U/L), and RNasin (1 L) in dark. The mixture was incubated at 42° C. for 2 hours for reverse transcription, and the reaction was terminated by adding 1.5 L of 20 mM EDTA. After the labeling, RNA was removed by NaOH treatment and neutralized by HCl. cDNA was immediately purified with a STRATAGENE™ PCR purification kit.

Microarray fabrication: Hundreds of genes chosen were amplified through polymerase chain reaction and quantified by spectrophotometry at 260 nm. All purified PCR products were adjusted to a concentration of 0.1 µg/µL in 50% dimethyl sulfoxide and spotted in duplicate on UltraGAP-STM™ coated slides (Corning®, Inc., Corning, N.Y.). After printing, the microarrays were UV cross-link at 300 mJoules and stored in the slide container in a desiccator at room temperature. The genes were listed in Table 3.

Microarray hybridization: Fluorescently labeled cDNA was denatured in the hybridization solution (5×SSC, 0.1% SDS and 25% formamide) at 100° C. for 5 min, cooled to ambient temperature, and deposited onto slides. The hybridization was carried out for 18 h at 42° C. After hybridization, the slides were successively washed in low-stringency (1×SSC and 0.1% SDS), medium-stringency (0.1×SSC and 0.1% SDS), high-stringency (0.1×SSC) buffer and finally were dried by compressed $N_2$.

Signal detection and data analysis: $N_2$-dried slides were immediately scanned on a GenePix® 4000B scanner (Axon Instruments®, Inc.) at the same laser power and sensitivity level of the photomultiplier for each slide. Raw fluorescence data were acquired (10-nm resolution), and subsequent processing and data visualization were performed in Microsoft Excel™. In order to compare the results of independent hybridization experiments, the local background signal was subtracted from the hybridization signal of each separate spot, and then divided by the housekeeping gene, β-actin. The final expression of each gene was represented in a mean of duplicates. The gene expression profiles of the Hep G2 cell cultured with and without GM-020 were then obtained. A group of genes upregulated or downregulated more than 2 fold in Hep G2 cultured with GM-020 to that cultured without the bacteria were selected. The results were shown in Table 4.

EXAMPLE 5

GM-020 for Treating Obesity

Animal model: Male ICR mice were purchased from National Laboratory Animal Center in Taiwan and raised alone in light for 12 hours and in dark for 12 hours at a temperature of 25±1° C. and a humidity of 60±5%. Food and water were supplemented sufficiently. The mice were divided into two groups. One was normal control group and the other was high energy group. The normal control group was fed with normal diet, and the high energy group was fed with high energy diet containing 48% dry feeding stuff, 8% corn oil and 44% condensed milk. The mice's body weights were measured every week. The high energy group was further divided into groups as listed below according treatment: (a) 1× of wood ear, (b) 1× of wood ear combined with GM-020, (c) GM-020, (d) 10× of wood ear, (e) 10× of wood ear combined with GM-020, (f) negative control treated with normal saline, and (g) positive control treated with PPA. The differences in body weight between before and after feeding high energy diet were shown in Table 6, wherein ** represented for $p<0.01$; $^a$ for negative control; $^b$ for positive control; $^c$ for 1× of wood ear; $^d$ for 10× of wood ear; $^e$ for GM-020; $^f$ for 1× of wood ear combined with GM-020; and $^g$ for 10× of wood ear combined with GM-020.

TABLE 6

| Group | Weight (%) |
| --- | --- |
| Normal Control | 12.25 ± 1.80 |
| Negative Control | 20.93 ± 2.27 |
| Positive Control | 20.43 ± 1.35 |
| 1 X of wood ear | 22.45 ± 1.46 |
| 10 X of wood ear | 18.45 ± 1.03 |
| GM-020 | 19.23 ± 1.75 |
| 1 X of wood ear combined with GM-020 | 21.37 ± 1.05 |
| 10 X of wood ear combined with GM-020 | 22.78 ± 0.67 |
| P value | 0.000**$^{a,b,c,d,e,f,g}$ |

The data were analyzed with Kruskal Wallis H Test, and normal control group was taken as a baseline for Dunnett Test. After 4 weeks, the body weight average of the high energy group was significantly higher than that of the normal control group ($p<0.01$).

Treatment with GM-020 and/or wood ear: The normal control group was fed with normal diet continuously. The treatments were administrated twice a day. The dosage of PPA was 4.875 mg each time. In the meal of 1× of wood ear, there was 15.6 mg of wood ear in 3 g diet, and in the meal of 10× of wood ear, there is 156 mg of wood ear in 3 g diet. The dosage of GM-020 was $10^9$ CFU/mL.

Figure 4:
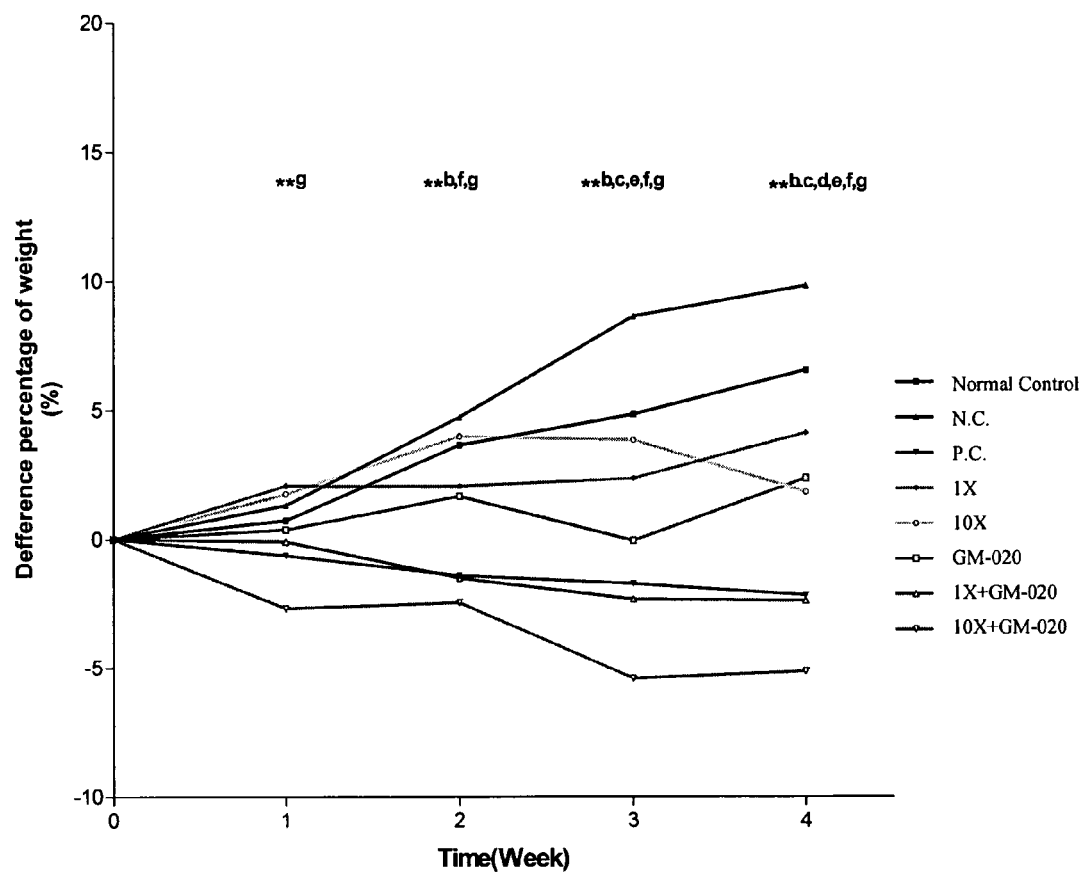
FIG. 4 illustrates the differences in body weight in the animal model treated with GM-020 or/and wood ear according to Example 5; wherein ** represents for $p<0.01$; [a] for negative control; [b] for positive control; [c] for 1× of wood ear; [d] for 10× of wood ear; [e] for GM-020; [f] for 1× of wood ear combined with GM-020; and [g] for 10× wood ear combined with GM-020.

Body weight difference: After treated for 4 weeks, blood samples were collected from the tails for biochemical assay. The data were analyzed with Kruskal Wallis H Test, and normal control group was taken as a baseline for Dunnett Test. The results were shown in FIG. 4.

After treating for one week, the group of 10× of wood ear combined with GM-020 had a significant decrease in body weight compared with the negative control group. After 2 weeks, the group of positive control, the group of 1× of wood ear combined with GM-020, and the group of 10× of wood ear combined with GM-020 had a significant decrease in body weight compared with the negative control group. After 3 weeks, the group of positive control, the group of 1× of wood ear, the group of GM-020, the group of 1× of wood ear combined with GM-020, and the group of 10× of wood ear combined with GM-020 had a significant decrease in body weight compared with the negative control group. The results demonstrate that GM-020 and wood ear is effective in treating obesity.

Differences of lipid tissue weight around the testicle: The mice were sacrificed, and the lipid tissues around the testicle were taken and weighted. The data were analyzed with Kruskal Wallis H Test, and that of the normal control group was taken as a baseline for Dunnett Test. The results were shown in FIG. 5.

Figure 5:
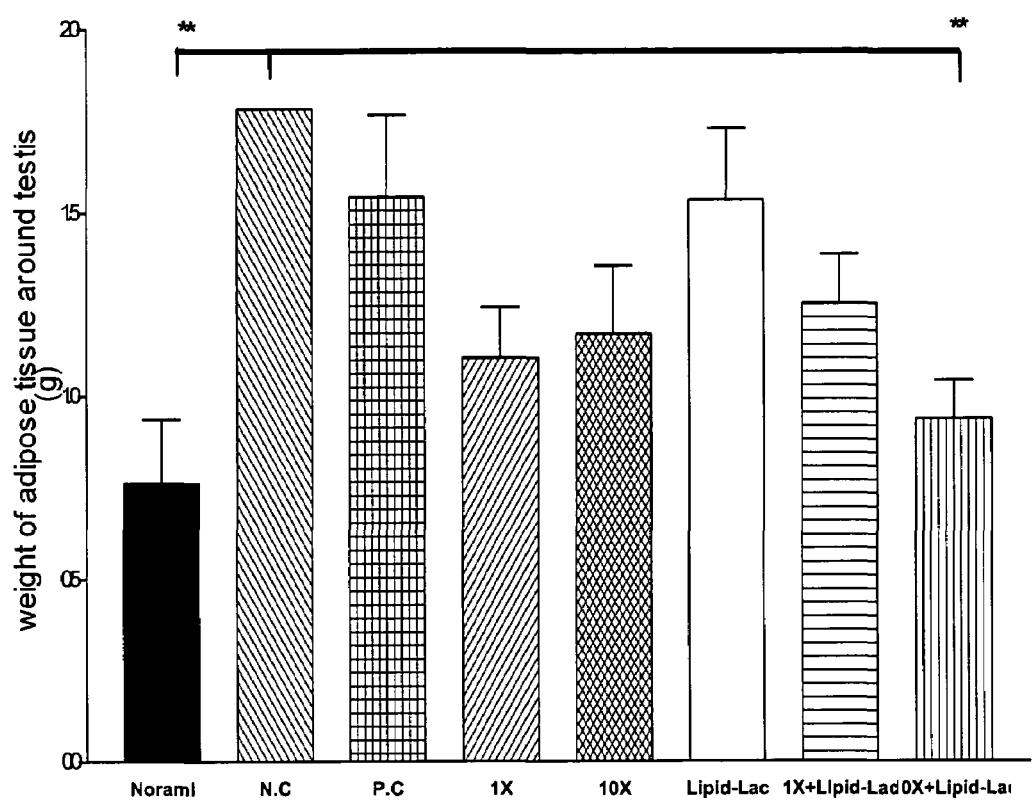
FIG. 5 illustrates the differences in lipid tissue weight around the testicle in the animal model treated with GM-020 or/and wood ear according to Example 5; wherein ** represents for $p<0.01$; [a] for negative control; [b] for positive control; $^c$ for 1× of wood ear; $^d$ for 10× of wood ear; $^e$ for GM-020; $^f$ for 1× of wood ear combined with GM-020; and $^g$ for 10× of wood ear combined with GM-020.

According to FIG. 5, only the group of positive control and the group 10× of wood ear combined with GM-020 showed a significant decrease compared with the negative control group.

Differences of lipid tissue weight around the kidney: The mice were sacrificed, and the lipid tissues around the kidney were taken and weighted. The data were analyzed with Kruskal Wallis H Test, and that of the normal control group was taken as a baseline for Dunnett Test. The results were shown in FIG. 6.

Figure 6:
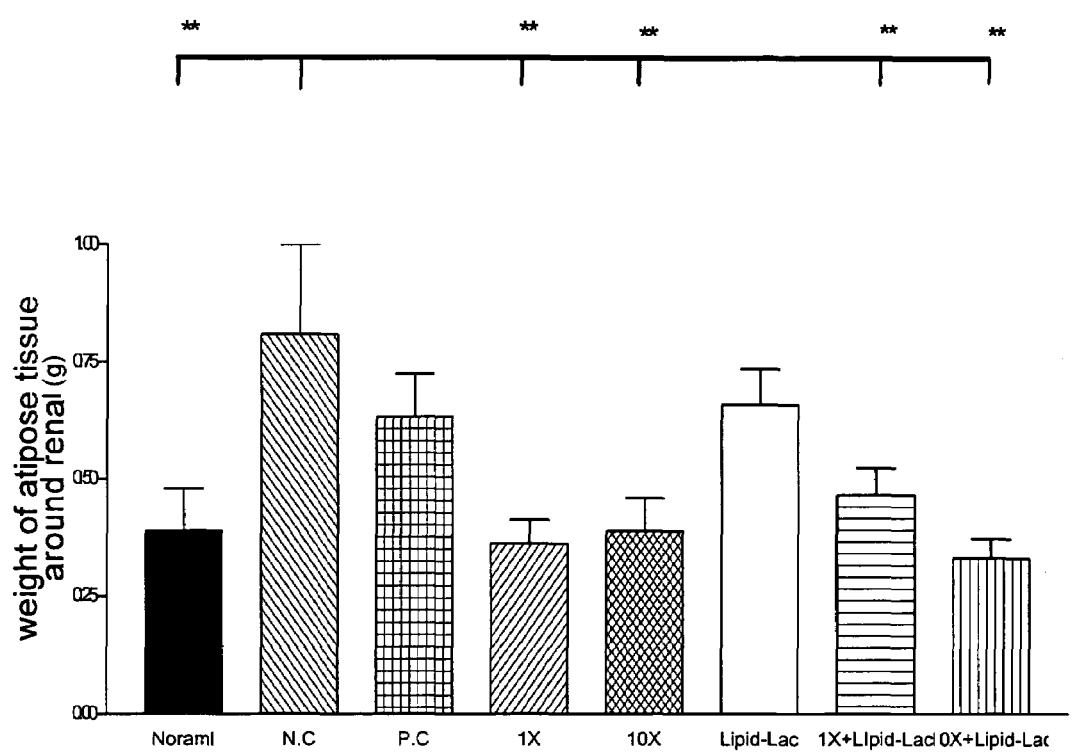
FIG. 6 illustrates the differences in lipid tissue weight around the kidney in the animal model treated with GM-020 or/and wood ear according to Example 5; wherein ** represents for p<0.01; $^a$ for negative control; $^b$ for positive control; $^c$ for 1× wood ear; $^d$ for 10× wood ear; $^e$ for GM-020; $^f$ for 1× wood ear combined with GM-020; and $^g$ for 10× wood ear combined with GM-020.

According to FIG. 6, the group of 1× of wood ear, the group of 10× of wood ear, the group of 1× wood ear combined with GM-020, and the group of 10× of wood ear combined with GM-020 had a significant decrease compared with negative control group. On the other hand, the group of positive control, the group of GM-020, and the negative control showed little difference.

Serum concentration of fat metabolites: Blood samples were collected from the tails for biochemical assay. The blood samples were stayed at room temperature for 1 hour and centrifuged at 2,500 rpm for 10 minutes. The upper layer of serum was taken for assay.

The concentration of triacylglycol (TG) of each group was assayed with TRIGLYCERIDES GPO LIQUID REAGENT™ (ASK®, Taiwan) and the absorption was measured with Autoanalyzer Hitachi™ 7150. The concentration of total cholesterol (CHOL) was assayed with CHOLESTEROL LIQUID REAGENT™ (ASK®, Taiwan), and the absorption was measured with Autoanalyzer Hitachi™ 7150. The concentration of HDL-C and LDL-C were assayed according to selectively inhibition method and enzyme determination (Unichem™, Japan) and the absorption was measured with Autoanalyzer Hitachi™ 7150.

The data were analyzed with Kruskal Wallis H Test, and that of the normal control group was taken as a baseline for Dunnett Test. The results were shown in Table 7; wherein represented for $p<0.01$; $^a$ for negative control; $^b$ for positive control; $^c$ for 1× of wood ear; $^d$ for 10× of wood ear; $^e$ for GM-020; $^f$ for 1× of wood ear combined with GM-020; and $^g$ for 10 × wood ear combined with GM-020.

TABLE 7

| Group | CHOL | TG | HDL | LDL |
|---|---|---|---|---|
| Negative Control | 232.00 ± 16.88 | 86.60 ± 22.40 | 126.39 ± 7.37 | 11.21 ± 1.40 |
| Normal Control | 135.80 ± 6.67 | 120.00 ± 20.35 | 86.90 ± 3.14 | 4.22 ± 0.56 |
| Positive Control | 219.08 ± 11.22 | 75.83 ± 9.93 | 123.19 ± 4.20 | 10.04 ± 0.93 |
| 1 X of wood ear | 182.50 ± 8.24 | 82.08 ± 7.32 | 100.57 ± 3.58 | 12.39 ± 1.03 |
| 10 X of wood ear | 176.83 ± 9.84 | 63.92 ± 4.62 | 93.51 ± 6.02 | 9.74 ± 1.07 |
| GM-020 | 204.75 ± 8.90 | 96.56 ± 10.20 | 121.64 ± 8.47 | 14.04 ± 3.10 |
| 1 X of wood ear combined with GM-020 | 190.08 ± 4.85 | 55.75 ± 4.38 | 105.38 ± 3.10 | 10.83 ± 1.51 |
| 10 X of wood ear combined with GM-020 | 164.20 ± 8.64 | 57.30 ± 4.61 | 97.93 ± 5.42 | 8.04 ± 0.94 |
| P value | 0.000**[a,c,d,f,g] | 0.000 | 0.000**[a,c,d,f,g] | 0.014*[a] |

The group of 1× of wood ear combined with GM-020 and the group of 10× of wood ear combined with GM-020 had a lower serum concentration of triacylglycol than the negative control group. On the other hand, the group of 1× of wood ear, the group of 10× of wood ear and the group of GM-020 had a little difference compared with the negative control group. Besides, the group of 1× of wood ear, the group of 10× of wood ear, the group of 1× wood ear combined with GM-020, and the group of 10× of wood ear combined with GM-020 had lower serum concentrations of total cholesterol and HDL-C. As to the concentration of LDL-C, every group except the normal control showed little difference.

Liver concentration of fat metabolites: The mice were sacrificed, and the right lobe of liver was taken. The fat was extract according to the conventional method.

For each sample, the concentration of triacylglycol (TG) and total cholesterol (CHOL) were assayed as mentioned above.

The data were analyzed with Kruskal Wallis H Test, and that of normal control group was taken as a baseline for Dunnett Test. The results were shown in Table 8; wherein ** represented for $p<0.01$; [a] for negative control; [b] for positive control; [c] for 1× of wood ear; [d] for 10× of wood ear; [e] for GM-020; [f] for 1× of wood ear combined with GM-020; and [g] for 10× of wood ear combined wtih GM-020.

TABLE 8

| Group | CHOL | TG |
|---|---|---|
| Negative Control | 25.75 ± 2.17 | 135.00 ± 11.92 |
| Normal Control | 21.80 ± 0.58 | 65.60 ± 6.56 |
| Positive Control | 26.75 ± 1.48 | 103.58 ± 11.41 |
| 1 X of wood ear | 20.75 ± 0.85 | 85.50 ± 3.76 |
| 10 X of wood ear | 22.00 ± 0.72 | 84.83 ± 8.56 |
| GM-020 | 19.44 ± 0.85 | 88.56 ± 6.41 |
| 1 X of wood ear combined with GM-020 | 21.25 ± 0.70 | 83.25 ± 6.27 |
| 10 X of wood ear combined with GM-020 | 20.90 ± 0.81 | 77.50 ± 7.82 |
| P value | 0.000**[c,e,f,g] | 0.004*[a,c,d,e,f,g] |

Each of the group of 1× of wood ear, the group of GM-020, the group of 1× of wood ear combined with GM-020, and the group of 10× of wood ear combined with GM-020 had a lower serum concentration of total cholesterol. As to triacylglycol, the group of 1× of wood ear, each of the group of 10× of wood ear, the group of 1× of wood ear combined with GM-020, and the group of 10× wood ear combined with GM-020 had a significant decrease.

Liver and kidney function assays: The blood samples were treated as described above.

For each sample, the concentration of creatinine was assayed according to Jaffe Reaction method (Unichem®, Japan) and the absorption was measured with Autoanalyzer Hitachi™ 7150. The concentration of GOT was assayed with GOT (ASAT) IFCC mod™. (HUMAN®, Germany) and the absorption was measured with Autoanalyzer Hitachi™ 7150. The concentration of GPT was assayed with GPT (ALAT) IFCC mod™. (HUMAN®, Germany) and the absorption was measured with Autoanalyzer Hitachi™ 7150. The concentration of uric acid (UA) was assayed according to uricase-peroxidase method (Unichem®, Japan) and the absorption was measured with Autoanalyzer Hitachi™ 7150.

The data were analyzed with Kruskal Wallis H Test, and that of the normal control group was taken as a baseline for Dunnett Test. The results were shown in Table 9; wherein ** represented for $p<0.01$; [a] for negative control; [b] for positive control; [c] for 1× of wood ear; [d] for 10× of wood ear; [e] for GM-020; [f] for 1× of wood ear combined with GM-020; and [g] for 10× of wood ear combined with GM-020.

TABLE 9

| Group | GOT | GPT | Creatinine | UA |
|---|---|---|---|---|
| Normal Control | 134.00 ± 23.11 | 72.67 ± 6.98 | 0.52 ± 0.04 | 2.66 ± 0.92 |
| Negative Control | 79.20 ± 6.22 | 49.00 ± 9.18 | 0.52 ± 0.02 | 3.90 ± 1.33 |

TABLE 9-continued

| Group | GOT | GPT | Creatinine | UA |
|---|---|---|---|---|
| Positive Control | 117.50 ± 12.95 | 47.00 ± 6.17 | 0.56 ± 0.03 | 2.42 ± 0.50 |
| 1 X of wood ear | 107.00 ± 14.77 | 37.33 ± 2.77 | 0.47 ± 0.02 | 5.20 ± 0.91 |
| 10 X of wood ear | 120.00 ± 15.78 | 57.42 ± 5.68 | 0.46 ± 0.02 | 2.88 ± 0.57 |
| GM-020 | 109.67 ± 17.30 | 36.22 ± 3.05 | 0.47 ± 0.03 | 1.96 ± 0.40 |
| 1 X of wood ear combined with GM-020 | 150.00 ± 21.71 | 44.91 ± 3.93 | 0.45 ± 0.02 | 2.12 ± 0.48 |
| 10 X of wood ear combined with GM-020 | 76.40 ± 13.5 | 37.50 ± 3.95 | 0.39 ± 0.03 | 2.10 ± 0.36 |
| P value | 0.072 | 0.002**[b,c,e,f,g] | 0.002**[g] | 0.006 |

The differences among the results of the groups are not significant. It was evidenced that the indexes of liver and kidney functions were not affected after the treatment of GM-020 and/or wood ear.

EXAMPLE 6

GM-020 for Treating Hypercholesterolemia

Animal model: Male hamsters were purchased from National Laboratory Animal Center in Taiwan and raised alone in light for 12 hours and in dark for 12 hours at a temperature of 25±1° C. and a humidity of 60±5%. Food and water were supplemented sufficiently. The mice were divided into two groups: one for normal control (NC) group and the other for cholesterol-enriched diet group. The normal control group was fed with normal diet, and the cholesterol-enriched diet group was fed with 2% cholesterol-enriched diet containing 24% protein, 14% fat, 2% cholesterol, 48% carbohydrate, 6% fiber, and 6% mineral and vitamin mixture.

Treatment with GM-020: The normal control group was fed with normal diet continuously. The treatments were administrated twice a day. The cholesterol-enriched diet group was further divided into groups as listed below according treatment: (a) $L.\ gasseri$, (b) GM-020, (c) $L.\ sporogenes$, and (d) negative control (Control) treated with normal saline. The dosage was $10^9$ CFU/mL each time.

Serum concentration of fat metabolites: Blood samples were collected from the periorbital veins for biochemical assay before and after the treatment. The blood samples were stayed at room temperature for 1 hour and centrifuged at 2,500 rpm for 10 minutes. The upper layer of serum was taken for assay.

For each sample, the concentrations of total cholesterol (CHOL), HDL-C, LDL-C, and triacylglycol (TG) were assayed as described above. The data were analyzed with Kruskal Wallis H Test, and that of normal control group was taken as a baseline for Dunnett Test. The differences in fat content between before and after feeding cholesterol-enriched diet were shown in Table 10, wherein * represented for $p<0.1$;  for $p<0.05$; * for $p<0.01$; [a] for negative control; [b] for $L.\ gasseri$; [c] for GM-020; [d] for $L.\ sporogenes$.

TABLE 10

| | HDL-C_0 | HDL-C_4 | LDL-C_0 | LDL-C_4 | CHOL_0 | CHOL_4 | TG_0 | TG_4 |
|---|---|---|---|---|---|---|---|---|
| NC | 117.6 ± 10.8 | 119.5 ± 11.5 | 105.4 ± 8.4 | 243.6 ± 25.2 | 398.8 ± 31.2 | 485.5 ± 70.4 | 421.0 ± 59.9 | 365.8 ± 65.9 |
| Control | 70.5 ± 3.6 | 64.9 ± 5.0 | 23.5 ± 1.3 | 20.8 ± 1.8 | 104.0 ± 4.1 | 96.8 ± 5.3 | 224.0 ± 23.1 | 180.7 ± 14.8 |
| L. gasseri | 141.3 ± 10.5 | 103.1 ± 3.8 | 179.4 ± 21.2 | 211.2 ± 23.9 | 531.6 ± 32.9 | 653.0 ± 45.1 | 585.8 ± 103.0 | 822.6 ± 59.1 |
| GM-020 | 108.8 ± 14.2 | 118.7 ± 8.4 | 106.9 ± 9.0 | 136.5 ± 19.8 | 412.0 ± 63.0 | 420.4 ± 53.0 | 483.3 ± 67.5 | 760.5 ± 98.7 |
| L. sporogenes | 104.9 ± 23.7 | 82.8 ± 3.0 | 127.1 ± 6.6 | 202.3 ± 11.6 | 414.5 ± 18.1 | 541.5 ± 51.9 | 439.5 ± 42.0 | 687.8 ± 131.0 |
| P Value | 0.008[a]** | 0.000[d]*** | 0.000[a,b]*** | 0.000[a,c]*** | 0.000[a]*** | 0.000[a]*** | 0.008[a]** | 0.000[b,c,d]*** |

According to the result, the cholesterol-enriched diet group showed significantly increase of CHOL, HDL-C, LDL-C, and TG after feeding cholesterol-enriched diet for 4 weeks when compared with the normal control group, and the subgroups of the cholesterol-enriched diet showed little difference between each other.

As to the TG, all the subgroups of the cholesterol-enriched diet group showed significantly larger than the normal control group after the treatment for 4 weeks.

Figure 7:
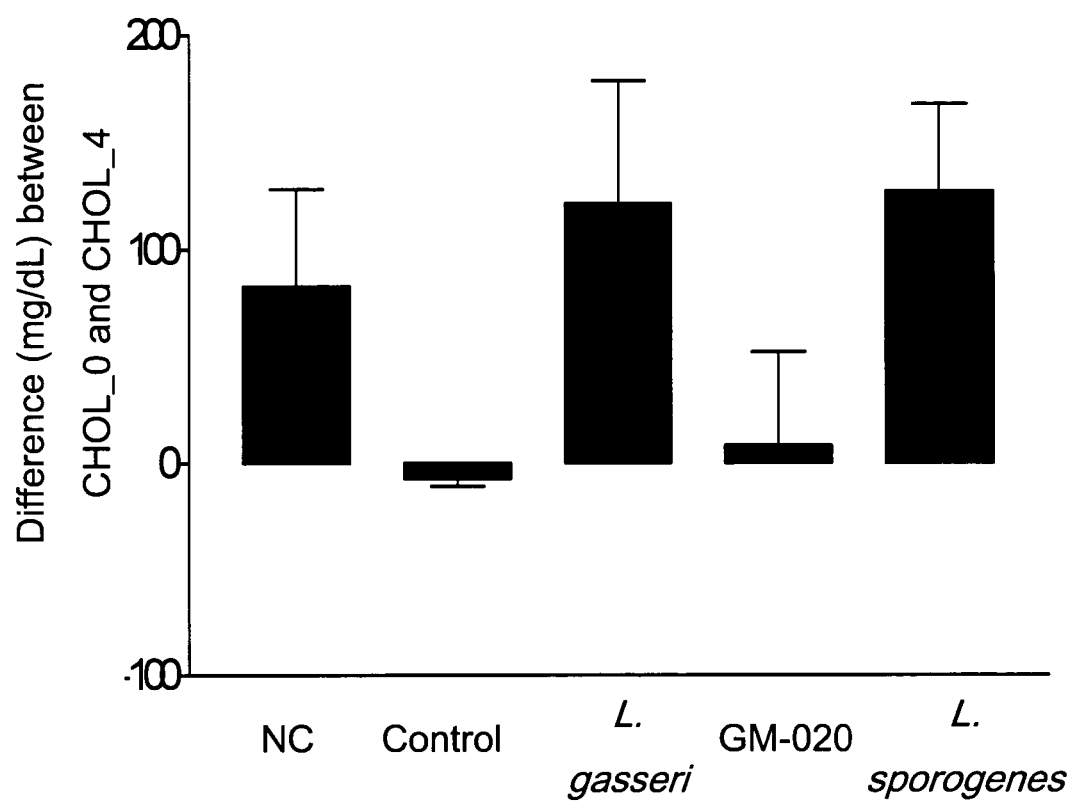
FIG. 7 illustrates the differences between the serum concentrations of total cholesterol between before (CHOL_0) and after (CHOL_4) treatment according to Example 6; wherein * represents for p<0.1;  for p<0.05; * for p<0.01.

As to CHOL, the groups of $L.\ gasseri$, $L.\ sporogenes$ and negative control showed significantly larger than the normal control group after the treatment for 4 weeks. On the other hand, the GM-020 group showed little increase compared with the normal control. The differences between before (CHOL_0) and after (CHOL_4) treatment were shown in FIG. 7. It was evidenced that GM-020 has an ability to lower serum concentration of total cholesterol.

As to HDL-C, the $L.\ sporogenes$ group showed significantly lower than the normal control group after the treatment for 4 weeks. However, the groups of $L.\ gasseri$, GM-020 and negative control showed little difference.

Figure 8:
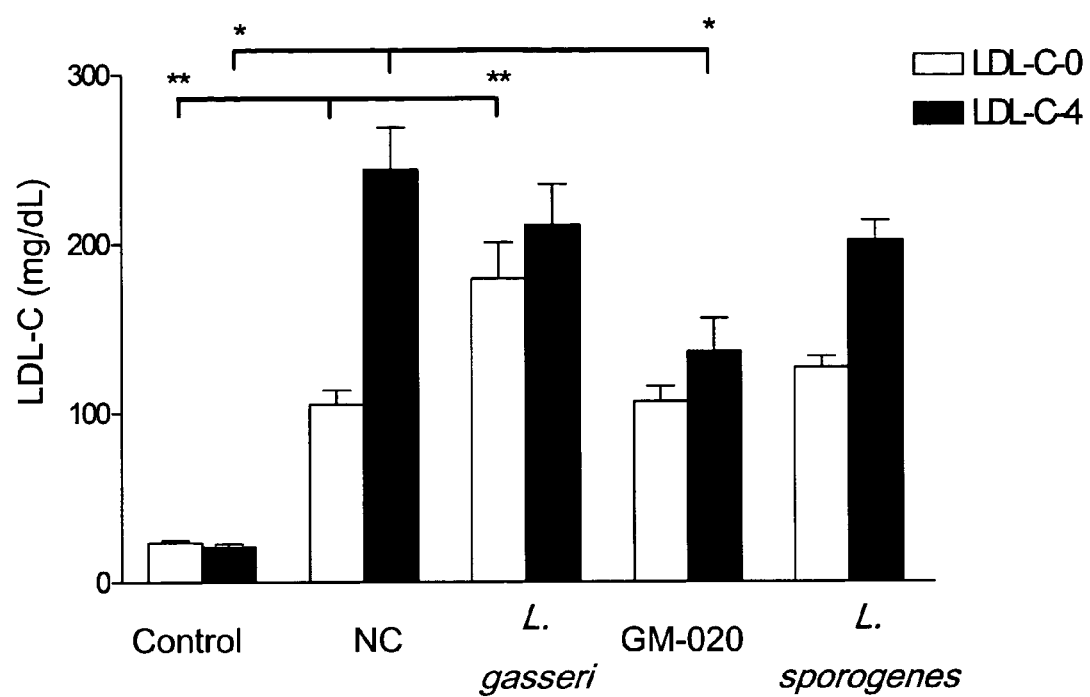
FIG. 8 illustrates the serum concentrations of LDL-C before (LDL-C_0) and after (LDL-C_4) treatment according to Example 6; wherein * represents for p<0.1;  for p<0.05; * for p<0.01.
Figure 9:
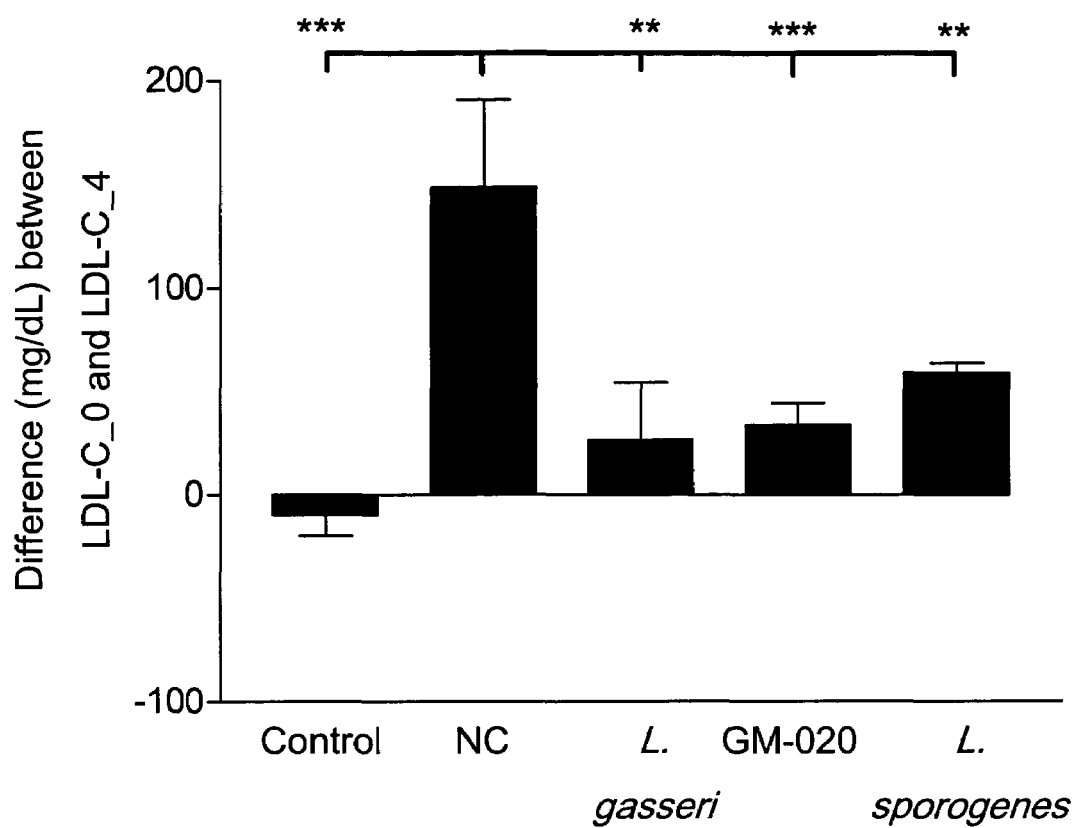
FIG. 9 illustrates the difference between the serum concentrations of LDL-C between before (LDL-C_0) and after (LDL-C/HDL-C_4) treatment according to Example 6; wherein * represents for p<0.1;  for p<0.05; * for p<0.01.

As to LDL-C, the serum concentration was shown in FIG. 8. The GM-020 group showed significantly decrease compared with the normal control ($p<0.1$). Besides, the groups of $L.\ gasseri$ and $L.\ sporogenes$ showed significantly ($p<0.05$) lower than the normal control group after the treatment for 4 weeks (referring to FIG. 9). It was evidenced that GM-020 has an ability to lower serum concentration of total cholesterol.

Figure 10:
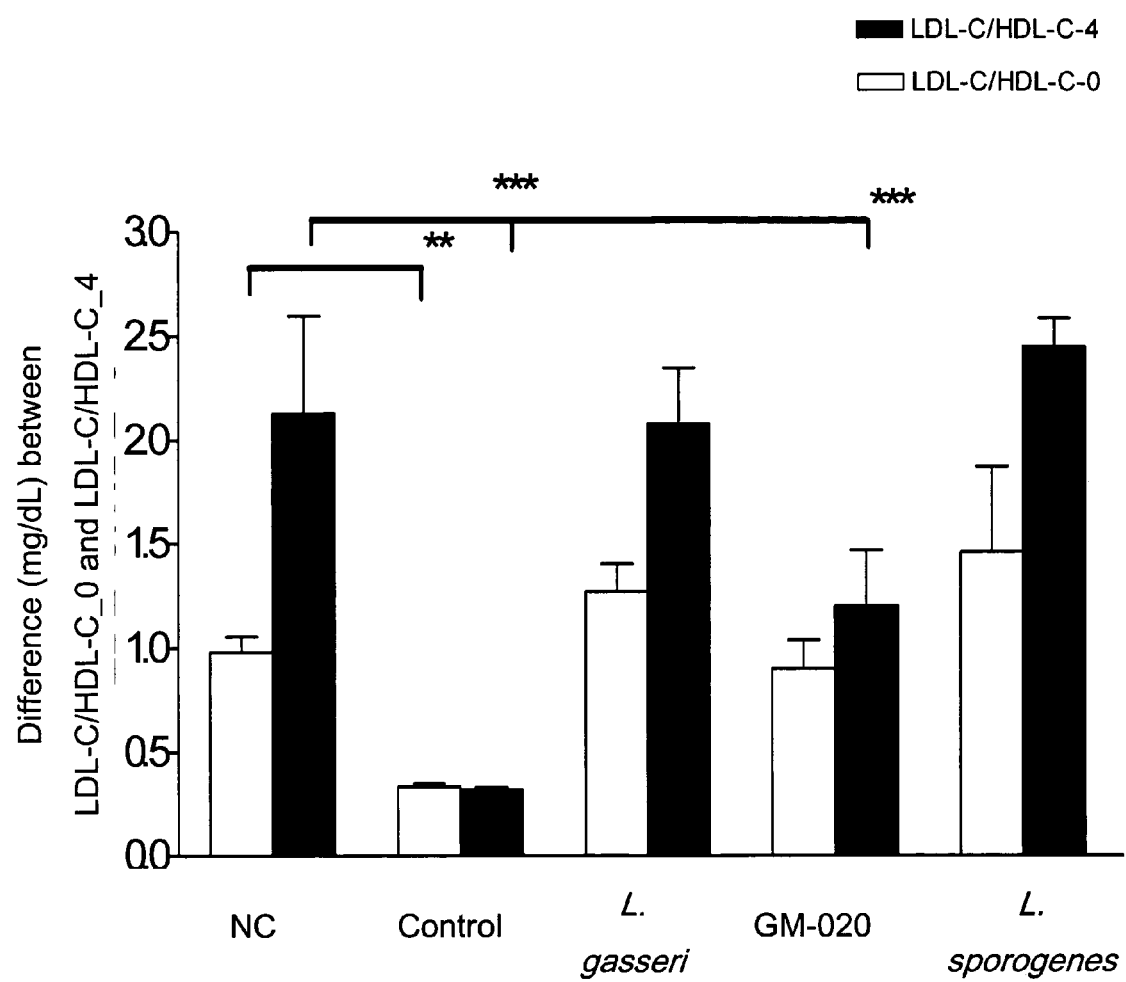
FIG. 10 illustrates the difference of the serum concentrations of LDL-C/HDL-C between before (LDL-C/HDL-C_0) and after (LDL-C/HDL-C_4) treatment according to Example 6; wherein * represents for p<0.1;  for p<0.05; * for p<0.01.

As to LDL-C/HDL/C, the ratio was shown in Table 11 and FIG. 10, wherein * represented for $p<0.1$;  for $p<0.05$; * for $p<0.01$; [a] for negative control; [b] for $L.\ gasseri$; [c] for GM-020; [d] for $L.\ sporogenes$. The data were analyzed with Kruskal Wallis H Test, and that of the normal control group was taken as a baseline for Dunnett Test.

TABLE 11

|  | LDL-C/HDL-C_0 | LDL-C/HDL-C_4 |
|---|---|---|
| NC | 0.98 ± 0.07 | 2.13 ± 0.47 |
| Control | 0.33 ± 0.02 | 0.32 ± 0.01 |
| L gasseri | 1.27 ± 0.13 | 2.08 ± 0.27 |
| GM-020 | 0.90 ± 0.13 | 1.20 ± 0.27 |
| L. sporogenes | 1.46 ± 0.42 | 2.44 ± 0.14 |
| P Value | $0.003^{a,*}$ | $0.000^{a,c,***}$ |

The GM-020 group showed a significant decrease compared with the normal control (p<0.001). It was evidenced that GM-020 has an ability to lower the value of LDL-C/HDL-C.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

What is claimed is:

1. An isolated microorganism of the strain *Lactobacillus rhamnosus* GM-020, deposited at the China Center for Type Culture Collection under CCTCC No.: CCTCC M 203098.

2. A composition comprising a suspension of the isolated microorganism strain according to claim 1.

3. A composition according to claim 2, which is used for treating obesity or a complication thereof, wherein the *Lactobacillus rhamnosus* GM-020 is gram-stain positive.

4. The composition according to claim 3 further comprising *Auricularia polytricha*.

5. The composition according to claim 3, comprising a dosage of *Lactobacillus rhamnosus* GM-020 of $10^9$ CFU/mL and wherein the complication is selected from the group consisting of hypercholesterolemia, atherosclerosis and coronary heart disease.

6. A composition for treating obesity and a complication thereof in a subject comprising the isolated microorganism according to claim 1 and *Auricularia polytricha*.

7. A method for treating obesity or a complication thereof in a subject comprising administrating said subject with a composition comprising the isolated microorganism according to claim 1.

8. The method according to claim 7, wherein the composition further comprises *Auricularia polytricha*.

9. A method for treating obesity and a complication thereof in a subject comprising administrating said subject with a composition comprising the strain according to claim 1 and *Auricularia polytricha*.

* * * * *

UNITED STATES PATENT AND TRADEMARK OFFICE
CERTIFICATE OF CORRECTION

PATENT NO. : 7,001,756 B1
APPLICATION NO. : 10/780601
DATED : February 21, 2006
INVENTOR(S) : Ching-Hsiang Hsu et al.

It is certified that error appears in the above-identified patent and that said Letters Patent is hereby corrected as shown below:

In Column 17, Claim 3, Line 59:
   Please replace "a complication thereof," with --hypercholesterolemia--

In Column 17, Claim 5, Lines 64-67:
   Please replace "CFU/mL and wherein the complication is selected from the group consisting of hypercholesterolemia, atherosclerosis and coronary heart disease." with --CFU/mL.--

In Column 18, Claim 6, Line 52:
   Please replace "a complication thereof" with --hypercholesterolemia--

In Column 18, Claim 7, Line 55:
   Please replace "a complication thereof" with --hypercholesterolemia--

In Column 18, Claim 7, Line 56:
   Please replace "administrating said" with --administrating to said-- and remove "with"

In Column 18, Claim 7, Lines 61-62:
   Please replace "a complication thereof" with --hypercholesterolemia--

In Column 18, Claim 7, Line 62:
   Please replace "administrating said" with --administrating to said--

In Column 18, Claim 7, Line 63:
   Please remove "with" and replace "strain" with --isolated microorganism--

Signed and Sealed this

Twenty-second Day of August, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 501
<212> TYPE: DNA
<213> ORGANISM: Lactobacillus rhamnosus

<400> SEQUENCE: 1

```
tcaggatgaa cgctggcggc gtgcctaata catgcaagtc gaacgagttc tgattattga      60
aaggtgcttg catcttgatt taattttgaa cgagtggcgg acgggtgagt aacacgtggg     120
taacctgccc ttaagtgggg gataacattt ggaaacagat gctaataccg cataaatcca     180
agaaccgcat ggttcttggc tgaaagatgg cgtaagctat cgcttttgga tggacccgcg     240
gcgtattagc tagttggtga ggtaacggct caccaaggca atgatacgta gccgaactga     300
gaggttgatc ggccacattg ggactgagac acggcccaaa ctcctacggg aggcagcagt     360
agggaatctt ccacaatgga cgcaagtctg atggagcaac gccgcgtgag tgaagaaggc     420
tttcgggtcg taaaactctg ttgttggaga agaatggtcg gcagagtaac tgttgtcggc     480
gtgacggtat ccaaccagaa a                                               501
```